United States Patent
Henneberry et al.

(10) Patent No.: US 6,797,684 B2
(45) Date of Patent: Sep. 28, 2004

(54) BIOSOLVENT COMPOSITION OF LACTATE ESTER AND D-LIMONENE WITH IMPROVED CLEANING AND SOLVATING PROPERTIES

(75) Inventors: Mark Henneberry, El Paso, IL (US); Joshua A. Snively, Winter Haven, FL (US); Gerald J. Vasek, Westmont, IL (US); Rathin Datta, Chicago, IL (US)

(73) Assignees: Vertec Biosolvents, Inc., Downers Grove, IL (US); Florida Chemical Co., Inc., Winter Haven, FL (US)

( * ) Notice: Subject to any disclaimer, the term of this patent is extended or adjusted under 35 U.S.C. 154(b) by 156 days.

(21) Appl. No.: 10/095,596

(22) Filed: Mar. 11, 2002

(65) Prior Publication Data

US 2003/0171241 A1 Sep. 11, 2003

(51) Int. Cl.$^7$ ............... C11D 17/00; C11D 17/08
(52) U.S. Cl. ............... 510/417; 510/365; 510/505
(58) Field of Search ................. 510/433, 417, 510/365, 505, 506; 134/38, 40

(56) References Cited

U.S. PATENT DOCUMENTS

| | | | |
|---|---|---|---|
| 5,334,331 A | | 8/1994 | Fusiak |
| 5,346,652 A | * | 9/1994 | Dotolo et al. ............ 510/118 |
| 5,360,580 A | | 11/1994 | Dotolo |
| 5,372,742 A | | 12/1994 | Bayless |
| 5,464,555 A | * | 11/1995 | Bayless ............... 510/174 |
| 6,066,606 A | | 5/2000 | Lu |
| 6,096,699 A | * | 8/2000 | Bergemann et al. ....... 510/201 |
| 6,191,087 B1 | | 2/2001 | Opre |
| 6,479,445 B1 | | 11/2002 | Machac, Jr. |

\* cited by examiner

*Primary Examiner*—Gregory Webb
(74) *Attorney, Agent, or Firm*—Welsh & Katz, Ltd.

(57) ABSTRACT

A solvent that is biodegradable, provides effective solvency for a broad range of tasks and is generally benign to human health is disclosed. This solvent is a mixture of a lactate ester and d-limonene.

12 Claims, No Drawings

BIOSOLVENT COMPOSITION OF LACTATE ESTER AND D-LIMONENE WITH IMPROVED CLEANING AND SOLVATING PROPERTIES

DESCRIPTION

1. Technical Field

The present invention relates to a solvent that is biodegradable and generally benign to human health, and more particularly to a mixture of a lactate ester and D-limonene; the mixture provides effective solvency for a broad range of tasks. This blended solvent is shown to provide effective performance for solvent applications, including cleaning applications, that provides for a non-toxic, cost effective alternative to commonly used toxic solvents from a renewable biological feedstock.

2. Background Art

Solvents derived from renewable biological feedstocks that are non-toxic and have very good environmental properties are becoming highly desirable for replacement of many halogenated or other toxic solvents.

Ethyl lactate and other lactate esters are environmentally benign, non-toxic solvents derived from renewable carbohydrates via fermentation and separations processes.

D-limonene is a biodegradable cleaning solvent and degreaser occurring in nature as the main component of citrus peel oil. These user-friendly characteristics encourage the use of d-limonene in solvent applications. However, d-limonene lacks some physical properties that limit its applicability to more widespread use.

D-limonene is not water-miscible and consequently not easily water-rinsable and is considered a non-aqueous cleaning solvent. D-limonene is a slow-drying solvent, that does not quickly evaporate off of surfaces to which it has been applied. The art does not teach how to address these problems with d-limonene that would permit extending the applicability of d-limonene as a solvent to a wider variety of solvent applications.

Lactate esters have complementary physical properties where d-limonene is lacking. Ethyl lactate is very water-miscible and has high solvating power to dissolve oxygenated chemicals and resins and to remove dried inks, paints, and coatings. However, ethyl lactate lacks adequate solvating power for very hydrophobic materials such as oils and greases that d-limonene is capable of solvating. Lactate esters, particularly ethyl and methyl lactate, are faster-drying solvents than d-limonene.

The blending of ethyl lactate with d-limonene in presence of other mixture components such as surfactants, or long chain alcohols or esters or polymers has been disclosed in the art.

U.S. Pat. No. 5,372,742, teaches blending ethyl lactate and d-limonene together with cetyl acetate and optionally with propylene glycol methyl ether acetate to give a liquid, non-aqueous cleaner composition that is well-suited as a fingernail polish remover.

U.S. Pat. No. 5,360,580 discloses a blend of d-limonene, N-methyl pyrrolidone, dibasic ester and cetyl acetate. That d-limonene mixture removes fingernail polish. The '580 patent teaches that lactate esters could be used to replace the d-limonene. The '580 patent does not teach blending d-limonene with lactate esters.

The art teaches solvent blend compositions with lactate ester or d-limonene blended with other components such as surfactants, longer chain alcohols, esters or ethers. However, the art does not teach or suggest how to modify the limiting properties of d-limonene are used. None of these show that just blending just these two biologically and renewable resource derived components, ethyl lactate and d-limonene could lead to solvent blend compositions with very desirable properties for many widespread applications.

D-limonene alone is often unsuitable for electronic and precision parts cleaning, where high purity solvents are typically used and water rinsability is often desired. Solvents used for these cleaning applications cannot leave residues. The addition of surfactants to solvents for use in electronic and precision parts cleaning is not acceptable for enhancing solvent rinsability, because surfactants tend to leave residue.

In many other cleaning applications, water miscibility is important. Being able to rinse a solvent-cleaned surface with water after the solvent cleaning step is preferable to rinsing with an organic solvent. Furthermore, aqueous rinses are often easier to handle and dispose of after application. Thus, water rinsability is highly desirable in a cleaning solvent for economic and environmental reasons.

Many pesticide and herbicide formulations require solvents that have very good solvating power for the active compounds as well as stability and dispersability. By having environmentally sound and non-toxic solvent blends to make pesticide and herbicide formulations could replace many of the currently used toxic solvents that are routinely sprayed on the crops in conjunction with the pesticides and herbicides.

A solvent is a substance that is generally capable of dissolving another substance, or solute, to form a uniformly dispersed mixture (solution) at the molecular or ionic level. Solvents are either polar (high dielectric constant) or non-polar (low dielectric constant). Water, the most common solvent, is strongly polar having a dielectric constant of 81. Hydrocarbon solvents are non-polar and are comprised of two groups, aliphatics such as alkanes and alcohols, and aromatics, which generally have a higher solvency power than aliphatics. Other organic solvent groups are esters, ethers, ketones, amines, nitrated hydrocarbons and halogenated hydrocarbons.

The chief uses of organic solvents include dissolution of coatings (paints, varnishes, and laquers), industrial and household cleaners, printing inks, and extractive processes. Because many solvents are flammable and toxic to health, there is a need to develop safer solvents for commercial use without sacrificing critical performance.

For decades industrial and household cleaning products have been utilized to provide certain tasks such as paint removers, ink removers, degreasers, etc. Solvents are also used to clean, maintain, and prepare wood, metal, masonry, natural and synthetic fabrics, plastic components, electronic components. Although providing the needs of these many and mission-critical tasks, most solvents generally, are toxic, thus posing a threat to health and to the environment. These environmental and health threats include ozone depleting air pollutants and water pollution that threaten aquatic organisms and drinking water supplies. Many of these solvents are carcinogenic and hazardous to health in general.

Although government, industry and the community at large are all relatively well informed to the dangers of toxic solvents, the dangers associated with the use of such solvents have not dramatically diminished their use. Safer handling, disposal, recycling, recovery and other responsible methods of dealing with toxic substances are improving. However, the availability of safer alternative solvents is still not wide spread, especially in second and third world countries, which is due, primarily, to the high cost of the solvent alternatives and because the majority of the environmentally safer solvent alternatives do not provide satisfactory performance.

In order for an "environmentally friendly" solvent alternative to gain wide spread acceptance, a solvent should meet several criteria. First, it should provide effective performance. Second, it should be economically viable and affordable. Third, it should be widely available and, of course, it should be non-toxic to the environment generally and humans specifically.

Several alternative solvents have been introduced by industry for decades, but in general do not meet the criteria stated above. Further, many of these solvents are not completely biodegradable, just less toxic.

A solvent described hereinafter provides high solvency performance while overcoming the toxicity issues associated with most other organic solvents. In addition, a contemplated solvent is biodegradable.

BRIEF SUMMARY OF THE INVENTION

The present invention contemplates an environmentally friendly solvent from renewable biological resources. This solvent consists essentially of d-limonene and lactate esters.

A contemplated solvent composition consists essentially of about x weight percent $C_1-C_4$ ester of lactic acid, where x is about 20 to about 80; and about 100-x weight percent of d-limonene (CAS Nos: 5989-27-5, 94266-27-4 and 68647-72-3).

In one preferred embodiment, the composition comprises:

(A) about 20 to about 40 weight percent of a $C_1-C_4$ ester of lactic acid; and (B) about 100-20 to 100-40 weight percent of d-limonene.

In each of the embodiments of the invention, the particularly preferred $C_1-C_4$ ester of lactic acid is the ethyl ester so that ethyl lactate is also particularly preferred.

The present invention has several benefits and advantages.

One benefit of the invention is that a contemplated composition is much safer than a halogenated organic solvent.

An additional advantage of the present invention is that the cleaning solvent is partially miscible with water, and thus can be removed with water rinsing, including high pressure water. This rinsing factor can offer some industrial advantages that do not exist with traditional cleaning solvents.

Yet another benefit of a preferred embodiment of the present invention is that it is biodegradable, non-toxic and is derived from renewable biological feedstocks.

Still further benefits and advantages will be apparent to the skilled worker from the discussion that follows.

DETAILED DESCRIPTION OF THE INVENTION

The present invention contemplates a d-limonene composition that extends the applicability of d-limonene in a variety of solvent applications by moderating the physical properties through mixture with $C_1-C_4$ lactate esters.

Even though both lactate esters and d-limonene solvents, individually, have many successful applications, they lack properties for much broader range of applications. The mixtures disclosed herein provide much broader range of applications because of certain enhanced properties.

A contemplated composition consists essentially of a solvent blend of x weight percent (W/W) of a $C_1-C_4$ ester of lactic acid, and 100 minus x weight percent of d-limonene, where x is about 20 to about 80. This blended solvent provides several key beneficial properties not achieved separately nor in combination with other solvent blend candidates.

More specifically, a contemplated composition consists essentially of (A) x weight percent of a $C_1-C_4$ ester of lactic acid; and (B) 100-x weight percent of d-limonene.

The $C_1-C_4$ ester of lactic acid is preferably an ethyl ($C_2$) ester. Exemplary $C_1-C_4$ alcohols that can comprise the $C_1-C_4$ ester portion of a lactate ester include methanol, ethanol, propanol, isopropanol, allyl alcohol, butanol, 3-buten-1-ol, t-butanol and sec-butanol. Technical grade ethyl lactate is commercially available Vertec Biosolvents, Inc. (Downers Grove, Ill.).

D-Limonene is commercially available from Florida Chemical Co., Inc. (Winter Haven, Fla.).

A contemplated composition contains essentially no surfactant or higher alcohols. The term "surfactant" is used following the nomenclature system of the *International Cosmetic Ingredient Dictionary*, 5$^{th}$ ed., J. A. Wenninger et al. eds., The Cosmetic, Toiletry, and Fragrance Association, Washington, D.C. (1993), usually followed by a chemical name and a trademark name of a particular product. Examples of surfactants are isotridecyl alcohol triethoxylate (Surfonic® TDA-3B, Huntsman Corp.), $C_9-C_{11}$ pareth-6 [polyethylene glycol ether of mixed synthetic $C_9-C_{11}$ fatty alcohols having an average of 6 moles of ethoxalate; Neodol® 91.6], $C_{11}-C_{15}$ pareth-59 [polyethylene glycol ether of mixed synthetic $C_{11}-C_{15}$ fatty alcohols having an average of 59 moles of ethoxalate; Tergitol® 15-S-59], nonoxynol-6 [polyethylene glycol (6) nonylphenyl ether; Tergitol® NP-6], nonoxynol-9 [polyethylene glycol (9) nonylphenyl ether; Tergitol® NP-9], and a modified alkanolamide alkanolamine [Monamine® 1255].

A contemplated composition contains essentially no higher alcohols. Examples of higher alcohols include $C_9-C_{15}$ alcohols.

A contemplated composition can also include a perfume (fragrance) to help mask the odor of the components and a colorant. These inactive ingredients are present, if at all, in minor amounts that do not exceed about 1 weight percent in aggregate. Although such inactive ingredients can be present in any contemplated composition, they are not preferred in a contemplated solvent.

Contemplated compositions are partially miscible with water. Water miscibility, which enhances water rinsability is advantageous, because it is easier to handle the cleaning solutions, dispose of them, dilute them and rinse them off of components. A biodegradable solution of the invention can be degraded in standard sewerage treatment plants, as opposed to special chemical waste handling procedures.

A contemplated composition is substantially free of added water. Thus, although some water can be present as a result of being an impurity of a constituent, water is typically not added to a composition, and a composition typically contains 5 weight percent water or less. The weight percent of the compositions described herein refers to the weight percent of the organic phase, and does not include the mass of any added water. A contemplated composition is also substantially free of halogenated compounds so that only contaminating amounts of such materials are present.

The present invention is illustrated in the non-limiting examples that follow.

EXAMPLE 1

20 Weight Percent Ethyl Lactate to Remove Permanent Marker and Dried Ink

This example is focused on removal and cleaning of dried graphics inks, graffiti and such.

A blend of 20 percent (W/W) ethyl lactate (x is 20) and 80 percent (W/W) limonene cleaned dried graphics inks (red and black) from a painted (white) enamel surface (Exterior Security Sign made by Four Paws Products, Ltd., Hauppauge, N.Y. 11788). A 100 percent d-limonene solvent could not remove the dried inks.

A blend of 20 percent ethyl lactate and 80 percent d-limonene removed dried ink marker (Sanford brand Permanent Marker, made by Sanford Corporation, Bellwood, Ill. 60104) graffiti from a painted (white) enamel surface without leaving a shadow. A 100 percent d-limonene solvent could not remove the marker effectively without leaving a visible shadow.

EXAMPLE 2

50% Ethyl Lactate Solution to Solvate Carbofuran Organophosphate

This example shows a 50:50 composition of the invention that has enhanced solvating properties for a pesticide/herbicide relative to d-limonene. The composition has the ability to readily dissolve active pesticide/herbicide compounds.

A 50% (W/W) ethyl lactate and 50% (W/W) d-limonene solution composition, where x is 50, dissolved a technical grade carbofuran organophosphate (solid at room temperature) without heating the material and under mild agitation. Solutions in concentration range of 10 to 20% w/w of the organophosphate could be prepared. The carbofuran organophosphate was 98% pure technical grade.

Many traditional solvents and blends for this application use aromatic hydrocarbons, glycol ethers, N-methyl pyrrolidone and others and require heating and prolonged agitation.

D-limonene alone did not have the solvating power to adequately dissolve this material.

EXAMPLE 3

50% Ethyl Lactate Solution to Solvate Pyrethrin

This is a further example showing enhanced solvating properties relative to d-limonene and ability to readily dissolve active pesticide/herbicide compounds of a solution according the present invention where x is 50.

A 50% (W/W) ethyl lactate and 50% (W/W) d-limonene readily dissolved a technical grade pyrethrin, Bifenthrin™ (manufactured by FMC; solid at room temperature) without heating the material under prolonged agitation. The technical grade pyrethrin, Bifenthrin™, was 95.05% pure technical grade.

Solution compositions of about 10 to 20% (w/w) could be achieved. Many traditional solvents used for this application function require heating and prolonged agitation.

Although d-limonene alone did dissolve this material, it did so with prolonged agitation and heating and achieved only half of the concentration that was achieved with the blend where x is 50. The use of crop spray formulations using the 50% (W/W) ethyl lactate and 50% (W/W) d-limonene are useful for relatively high concentrations of Bifenthrin™ without the risk of the Bifenthrin™ falling out of solution.

EXAMPLE 4

Enhancement of Grease- and Oil-Removing Properties of Ethyl Lactate

These examples show the enhanced ability relative to ethyl lactate of the solvent blend to clean and remove oils and greases from contaminated surfaces and then enabling further cleaning by water rinse alone.

Pre-weighed glass bottles were coated with a thin film of contaminating oil. The contaminating oil for this example was equal part blend of three commonly available oils used widely—motor oil (SAE 20/50), 2-stroke engine oil and hydraulic jack oil.

A known weight of the solvent or solvent blend was added to the bottle and the bottle was shaken for about 2 minutes. The spent solvent was then drained until no further solvent droplets would come out even after much shaking. This bottle was then weighed and the mass of residue and the percent removal of the initial contaminant by the solvent action only, were calculated.

After treatment with the solvent or solvent blend (and weighing for the data point), a known weight of deionized water was added. The bottle was shaken for about two minutes and the water was drained shaking until no further droplets would come out. This bottle was then weighed and the mass of residue and the percent removal of the initial contaminant by the action of both the solvent and the subsequent water rinse were determined.

The cleaned surface was then touched and how it felt was recorded. The results are summarized in the following Table 1, where EL is Ethyl Lactate and d-L is d-limonene.

TABLE 1

| Solvent Composition (w/w %) | 100% EL | 80% EL 20% d-L | 50% EL 50% d-L | 20% EL 80% d-L | 100% d-L |
|---|---|---|---|---|---|
| Mass of initial contaminating film (g) | 0.268 | 0.325 | 0.402 | 0.371 | 0.368 |
| Mass of film after solvent action (g) | 0.115 | 0.095 | 0.094 | 0.065 | 0.055 |
| Removal by solvent action alone (%) | 57.1 | 70.8 | 76.6 | 82.5 | 85.1 |
| Mass of film after water rinse | 0.076 | 0.035 | 0.021 | 0.038 | 0.03 |
| Removal by both solvent and water rinse (%) | 71.6 | 89.2 | 94.8 | 89.8 | 91.8 |
| Feel of the cleaned surface to touch | Oily | Slight oily | Clean - no solvent or oil | Solvent | Solvent |

The data in the above table demonstrate that the solvent blend has much better cleaning and water rinsability properties than either solvent alone. D-limonene has better dissolution properties for these very hydrophobic oils, but after it is removed, the surface cannot be readily rinsed and further cleaned with water alone.

In many applications this feature of water rinsability and further cleaning ability is very desirable because of economical and environmental discharge reasons.

EXAMPLE 5

Water-Rinsable Removal of Chain Bar and Sprocket Oil

This example gives further evidence of the enhanced ability of the solvent blend to clean and remove oils and greases from contaminated surfaces and then enabling further cleaning by water rinse alone. The contaminating oil in this example was commonly-available chain bar and sprocket oil sold by McCullough corporation of Tuscon, Ariz. The experimental method was the same as outlined in Example 4, above. The results are summarized below in Table 2.

TABLE 2

| Solvent Composition (w/w %) | 100% Ethyl Lactate | 80% Ethyl Lactate 20% d-limonene |
| --- | --- | --- |
| Mass of initial contaminating film (g) | 0.350 | 0.273 |
| Mass of film after solvent action (g) | 0.148 | 0.097 |
| Removal by solvent action alone (%) | 57.7 | 78.8 |
| Mass of film after water rinse | 0.148 | 0.029 |
| Removal by both solvent and water rinse (%) | 57.7 | 89.4 |
| Feel of the cleaned surface to touch | Oily | V. Slight Oily |

EXAMPLE 6

Water-Rinsable Removal of Thread-Cutting Oil

This example gives further evidence of the enhanced ability of the solvent blend to clean and remove oils and greases from contaminated surfaces and then enabling further cleaning by water rinse alone. The contaminating oil in this example was commonly-available, sold by ACE Hardware Corporation of Oakbrook, Ill. This thread-cutting oil is viscous and contains sulfur for providing lubricity. The experimental method was the same as outlined in Example 4, above. The results are summarized in Table 3.

TABLE 3

| | 100% Ethyl Lactate | 80% Ethyl Lactate 20% d-Limonene |
| --- | --- | --- |
| Mass of initial contaminating film (g) | 0.338 | 0.298 |
| Mass of film after solvent action (g) | 0.097 | 0.068 |
| Removal by solvent action alone (%) | 71.3 | 77.2 |
| Mass of film after water rinse (g) | 0.089 | 0.046 |
| Removal by both solvent and water rinse (%) | 73.7 | 84.6 |
| Feel of the cleaned surface to touch | Oily | v. Slight oily |

The Examples above demonstrate the surprising advantages from the blending of d-limonene with ethyl lactate, without any additional additives. The blends of these two solvents have enhanced properties not possessed by either solvent alone. Consequently, these blends can broaden the applicability for these two environmentally sound, solvents derived from biological renewable resources.

From the foregoing, it will be observed that numerous modifications and variations can be effectuated without departing from the true spirit and scope of the novel concepts of the present invention. It is to be understood that no limitation with respect to the specific examples presented is intended or should be inferred. The disclosure is intended to cover by the appended claims all such modifications as fall within the scope of the claims.

What is claimed:

1. A composition consisting essentially of:
    (A) x weight percent of a $C_1$–$C_4$ ester of lactic acid; and
    (B) 100–x weight percent of d-limonene;
    wherein x is about 20 to about 80.
2. The composition according to claim 1 wherein said $C_1$–$C_4$ ester of lactic acid is the ethyl ester.
3. The composition according to claim 1 wherein x is about 30 to about 70.
4. The composition according to claim 3 wherein x is about 50.
5. A method of preparing an herbicide and/or pesticide solution comprising the steps of:
    (1) providing a composition consisting essentially of:
        (A) x weight percent of a $C_1$–$C_4$ ester of lactic acid; and
        (B) 100–x weight percent of d-limonene;
        wherein x is about 20 to about 80
    (2) dissolving an herbicide into the composition of step (1) to form an herbicide and/or pesticide solution.
6. The method according to claim 4 wherein said herbicide and/or pesticide is pyrethrin or carbofuran organophosphate.
7. A method of removing grease or oil from a surface comprising the steps of:
    (1) providing a surface upon which is grease or oil;
    (2) contacting the surface with a composition consisting essentially of:
        (A) x weight percent of a $C_1$–$C_4$ ester of lactic acid; and
        (B) 100–x weight percent of d-limonene;
        wherein x is about 20 to about 80;
    (3) rinsing the surface from step (2) with water to remove the composition and grease or oil from the surface.
8. The method according to claim 6 wherein x is about 30 to about 70.
9. The method according to claim 7 wherein x is about 50.
10. A method of removing paint from a surface comprising the steps of:
    (1) providing a surface upon which is paint or ink;
    (2) contacting the surface with a composition consisting essentially of:
        (A) x weight percent of a $C_1$–$C_4$ ester of lactic acid; and
        (B) 100–x weight percent of d-limonene;
        wherein x is about 20 to about 80;
    (3) rinsing the surface from step (2) with water to remove the composition and paint or ink from the surface.
11. The method according to claim 6 wherein x is about 30 to about 70.
12. The method according to claim 7 wherein x is about 50.

* * * * *